United States Patent [19]

Kaplan et al.

[11] Patent Number: 4,844,854

[45] Date of Patent: Jul. 4, 1989

[54] PROCESS FOR MAKING A SURGICAL DEVICE USING TWO-PHASE COMPOSITIONS

[75] Inventors: Donald S. Kaplan, Weston; Matthew E. Hermes, Norwalk; Ross R. Muth, Brookfield; John J. Kennedy, Stratford, all of Conn.

[73] Assignee: United States Surgical Corporation, Norwalk, Conn.

[21] Appl. No.: 117,465

[22] Filed: Nov. 5, 1987

Related U.S. Application Data

[60] Division of Ser. No. 99,635, Sep. 22, 1987, Pat. No. 4,744,365, which is a continuation of Ser. No. 860,302, Jul. 17, 1986, abandoned, which is a continuation of Ser. No. 586,686, Mar. 6, 1984, abandoned.

[51] Int. Cl.$^4$ .......................... B29C 71/02; A61F 2/02
[52] U.S. Cl. ................... 264/235; 128/335.5; 264/328.1; 264/331.21; 264/346; 525/411; 525/415
[58] Field of Search .................. 264/235, 85, 328.17, 264/328.1, 101, 331.11, 331.21, 346; 128/335.5; 525/411, 415

[56] References Cited

U.S. PATENT DOCUMENTS

| | | | |
|---|---|---|---|
| 3,878,284 | 4/1975 | Schmitt et al. | 264/205 |
| 4,128,612 | 12/1978 | Roth | 264/210.8 |
| 4,137,921 | 2/1979 | Okuzumi et al. | 128/335.5 |
| 4,157,437 | 6/1979 | Okuzumi et al. | 528/354 |
| 4,444,927 | 4/1984 | Borysko | 264/331.21 |
| 4,490,326 | 12/1984 | Beroff et al. | 264/331.21 |
| 4,523,591 | 6/1985 | Kaplan et al. | 128/334 R |
| 4,591,630 | 5/1986 | Gertzman et al. | 264/346 |

*Primary Examiner*—Jeffery Thurlow
*Attorney, Agent, or Firm*—Kenyon & Kenyon; Thomas R. Bremer

[57] ABSTRACT

An absorbable, annealed surgical device made from a multi-phase, polymeric composition derived from lactide and glycolide is disclosed. Preferably, the composition has two phases, both phases are continuous, the first phase has about 0 - about 25%m glycolide moieties, the overall composition has up to 45%m glycolide moieties, and the first phase constitutes at least 50% (and preferably not more than about 95%) by weight of the composition. The device has a high distortion temperature, good resistance to hot-wet creep, but yet loses tensile strength in vivo quickly. The composition per se is injection-moldable, can be annealed, and is not brittle.

13 Claims, No Drawings

PROCESS FOR MAKING A SURGICAL DEVICE USING TWO-PHASE COMPOSITIONS

This is a division of application Ser. No. 099,635 filed Sept. 22, 1987 now U.S. Pat. No. 4,744,365 which is a continuation of Ser. No. 860,302 filed July 17, 1986, now abandoned which is a continuation of Ser. No. 586,686 filed Mar. 6, 1984, now abandoned.

BACKGROUND OF THE INVENTION

Polymers and copolymers of, and surgical devices made from, lactide and/or glycolide and/or related compounds are well-known. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,773,919, 3,781,349, 3,784,585, 3,792,010, 3,797,499, 3,839,297, 3,846,382, 3,867,190, 3,875,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,245,904, 4,273,920, 4,275,813, 4,279,249, and 4,300,565, U.K. Pat. or Appln Nos. 779,291, 1,332,505, 1,414,600, and 2,102,827, D. K. Gilding et al., "Biodegradable polymers for use in surgery --polyglycolic/poly (lactic acid) homo-and copolymers: 1," *Polymer,* Volume 20, pages 1459-1464 (1979), and D. F. Williams (ed.), *Bicompatibility of Clinical Implant Materials,* Volume II, chapter 9: "Biodegradable Polymers" (1981). Multi-phase polymeric compositions are shown in Matsuo et al., "Fine Structures of Styrene-Butadiene Block Copolymer Films Cast from Toluene Solution," Polymer, Volume 10, pages 79-87 (1969). All of the foregoing documents are hereby incorporated by reference.

Some of those documents mention or discuss making lactide/glycolide/related compound polymers or copolymers of small particle size. See, e.g., U.S. Pat. Nos. 3,781,349 and 3,846,382.

Some of those documents mention or discuss multi-stage or sequential addition of monomers in making the lactide/glycolide/related compound polymers or copolymers. See, e.g., U.S. Pat. Nos. 3,268,486, 3,268,487, 3,784,585, 4,137,921, 4,157,437, 4,243,775, and 4,300,565.

Some of the documents first listed mention or discuss multi-phase or block systems containing the lactide/glycolide/related compound polymers or copolymers. See, e.g., U.S. Pat. Nos. 3,268,486, 3,268,487, 3,463,158, 3,773,919, 3,784,585, 3,875,937, 4,045,418, 4,057,537, 4,137,921, 4,157,437, 4,243,775, 4,279,249, and 4,300,565, U.K. Pat. No. 1,332,505, Gilding et al., and Williams.

Some of the documents first listed mention or discuss annealing, heat-treating, or post-treating surgical articles containing the lactide/glycolide/ related compound polymers or copolymers. See, e.g., U.S. Pat. Nos. 3,422,181, 3,626,948, 3,636,956, 3,772,420, 3,782,010, 3,797,499, 3,839,297, 3,878,284, 4,137,921, 4,157,437, 4,243,775, and 4,300,565, and U.K. Pat. or Appln Nos. 1,332,505, 1,414,600, and 2,102,827.

In particular, some of the documents first listed mention or discuss annealing, heat-treating, or post-treating surgical articles made of poly(lactide/glycolide) copolymers made by multi-stage or sequential addition of the monomers. See, e.g., U.S. Pat. Nos. 4,137,921, 4,157,437, 4,243,775, and 4,300,565. In those documents, glycolide moieties constitute more than 50% by weight of the lactide/glycolide copolymers.

It is known that annealing polymers, copolymers, and surgical devices made from lactide and/or glycolide and/or related compounds increases the crystallinity and in vivo tensile strength retention of the polymers, copolymers, and surgical devices. It is also known that the greater the crystallinity, the longer such polymers, copolymers, and surgical devices retain their in vivo tensile strength. See some of the documents first listed, e.g., U.S. Pat. No. 3,636,956 (particularly column 2, line 43 et seq.), U.S. Pat. No. 4,137,921 (particularly column 9, lines 61-64), U.K. Appln. No. 2,102,827, and Williams (particularly pages 222-224). It is also known that increasing the crystallinity of such polymers and copolymers makes them more brittle and, thus, decreases their utility as injection molded surgical devices.

SUMMARY OF THE INVENTION

It has now been found that certain two-phase compositions derived from lactide and glycolide in which lactide moieties predominate have a remarkable and unexpected balance of desirable properties. Those properties include lack of brittleness and the ability to be injection molded and annealed. The properties of the composition, in turn, make it possible to injection mold surgical devices (e.g., staples, clips) from the composition and to anneal those devices to obtain devices having a remarkable and unexpected balance of desirable properties.

A problem with substantially amorphous one-phase poly(lactide/glycolide) devices wherein lactide moieties predominate is their occasionally low distortion temperature. (Substantially amorphous one-phase poly(lactide/glycolide) devices and compositions therefor are disclosed in commonly-assigned U.S. pat. appln. Ser. No. 436,056, filed Oct. 22, 1982, which is hereby incorporated by reference.) Thus, even the temperature on an extremely hot summer day in Arizona, for example, may be sufficient to cause such devices to deform slightly. Annealing such devices often deforms them so significantly (even if held in a mold during annealing) that they are no longer useful as surgical devices.

Surprisingly, as compared to a substantially amorphous, one-phase poly(lactide/glycolide) device of a given composition, the new annealed, two-phase device of the same overall composition has a much higher distortion temperature but essentially the same in vivo rate of loss of tensile strength. Thus, the present composition makes it possible to increase the resistance to thermal distortion of poly(lactide/glycolide) surgical devices without adversely affecting their rate of loss of tensile strength. The new devices also have surprising resistance to hot-wet creep. Also surprising and contrary to the suggestions of the art is that the step of annealing the new two-phase composition increases its crystallinity and tensile strength but decreases (not increases) the time required for it to lose tensile strength in vivo. Other advantages of this invention will be apparent to one skilled in the art.

In one aspect, the present invention relates to an absorbable, annealed surgical device of a multi-phase polymeric composition derived from lactide and glycolide, the first phase having about 0 - about 25%m glycolide moieties and about 75 - about 100%m lactide moieties and the other phases having glycolide and lactide moieties in amounts such that the composition overall has up to 45%m glycolide moieties, wherein the first phase constitutes at least 50% (and preferably not more than about 95%) by weight of the annealed surgical device. As the glycolide moiety content of the first phase approaches zero, the composition tends to become brittle. At some point the material will be too brittle for forming useful surgical devices. The exact lower limit of useful glycolide moiety content is not known.

In another aspect, the present invention relates a process for making a surgical device comprising the steps:

(a) polymerizing a first monomer mixture containing a predominant amount of lactide until the polymerization is substantially complete, thereby forming a first polymer;

(b) adding to the first polymer (with or without prior recovery and purification of the polymer) a second monomer mixture containing glycolide and polymerizing the second monomer mixture in the presence of the first polymer, thereby forming a second polymer having two phases;

(c) recovering the final polymer from the final polymerization stage (with or without purification of the polymer);

(d) forming a surgical device from the final polymer; and (e) annealing the surgical device;

(f) the quantities of monomers being chosen so that (i) the first phase of the final polymer has from about 0 - about 25%m glycolide moieties and about 75 - about 100%m lactide moieties, (ii) the final polymer overall has up to 45%m glycolide moieties, and (iii) the first phase constitutes at least 50% (and preferably not more than about 95%) by weight of the surgical device.

In another aspect, the present invention relates to a process for making a surgical device comprising the steps:

(a) preparing a first polymer containing about 0 - about 25%m glycolide moieties and about 75 - about 100%m lactide moieties;

(b) intimately mixing with the first polymer, particles of a second polymer containing a predominant amount of glycolide moieties, thereby forming a two-phase polymeric composition wherein the first phase constitutes at least 50% (and preferably not more than about 95%) by weight of the two-phase composition;

(c) forming the surgical device from the two-phase polymeric composition; and (d) annealing the surgical device.

In another aspect, the present invention relates to an annealable, injection-moldable lactide/glycolide polymeric composition having at least two phases wherein the first phase contains about 0 - about 25%m glycolide moieties and the other phases contain glycolide moieties in amounts such that the overall composition contains up to 45%m glycolide moieties and wherein the first phase constitutes at least 50% (and preferably not more than about 95%) by weight of the polymeric composition.

As used herein, "%m" means mole percent and "moiety" means that portion of a polymer derived from a particular monomer. Thus, a "glycolide moiety" of a polymer is a portion of the polymer derived from a starting glycolide monomer. As used herein, "substantially amorphous" means having 10% or less crystallinity (see, e.g., U.S. Pat. No. 3,878,284, column 3, lines 16–18). "Distortion temperature" means the temperature at which the dimensions of a surgical device start to change significantly because of flow of the material of the surgical device.

DETAILED DESCRIPTION OF THE INVENTION

The glycolide and lactide employed in making the new two-phase composition can be obtained commercially or may be made using known techniques. A preferred way of making the glycolide is as follows. Hydroxyacetic acid (glycolic acid) is heated under nitrogen to 180° C. to remove water. Pressure is then reduced and heating is continued for two hours to yield a prepolymer of polyglycolic acid, which is recovered and powdered.

The prepolymer is heated in the presence of $Sb_2O_3$ at 275° C. under low pressure with an argon purge and stirring. The prepolymer cracks and glycolide is distilled over and recovered in a cold vacuum receiver. Any purification technique that yields pure enough monomers may be used. Preferably, the glycolide is purified by conventional techniques, such as distillation, crystallization, and sublimation.

L-lactide is used alone or in combination with a small amount of the DL racemer. The amount of DL racemer, if used, should be low enough so that crystallization of the lactide-rich phase is not inhibited. L-lactide is purified by crystallization from toluene solution. The DL racemer, if used, is purified by crystallization from ethyl acetate.

The preferred two-phase polymeric lactide/glycolide composition of this invention has a lactide-rich phase having about 0 - about 25%m glycolide moieties and a glycolide-rich phase containing lactide and glycolide in amounts such that the composition overall contains up to 45%m glycolide moieties wherein the lactide-rich phase constitutes at least 50% by weight of the two-phase composition. Preferably, the lactide-rich phase has 10–20% m glycolide moieties and the composition overall has 30–45%m glycolide moieties. Most preferably, the lactide-rich phase has about 10% m glycolide moieties and the composition overall has about 35%m glycolide moieties.

The two-phase composition of this invention will either comprise a continuous lactide-rich phase interpolymerized with a continuous glycolide-rich phase or will comprise a continuous lactide-rich phase having dispersed throughout it discrete particles of a glycolide-rich phase. The former (continuous/continuous) is preferred and may be thought of as a limiting case of the latter (continuous/discrete), wherein the glycolide-rich particles are close enough to each other to be a continuous phase. In the continuous/discrete case, the lactide-rich phase is the matrix or continuous phase and the glycolide-rich dispersed particles together constitute the dispersed phase. In both cases, particles of a polymer containing glycolide moieties in a separate phase are distributed throughout a lactide-rich continuous phase. "Lactide-rich" phase and "glycolide-rich" phase mean containing a predominant amount of lactide moieties and containing a predominant amount of glycolide moieties, respectively.

The interpolymer two-phase polymeric compositions of this invention (continuous/continuous) may be made by polymerizing in a first stage a first monomer mixture, adding to the resulting polymer a second monomer mixture, and then in a second stage polymerizing the second monomer mixture while in intimate contact with the polymer of the first stage. Electron scanning micrographs of these compositions show that each phase is continuous, that is, the minor, glycolide-rich phase is continuously interpolymerized within the major lactide-rich phase. Any suitable polymerization technique may be used. See, for example, those disclosed in the documents listed in the Background of The Invention, above. There are two general polymerization schemes for making the interpolymer compositions of this invention.

First, the polymer resulting from the first-stage polymerization may be recovered, purified, and stored (if necessary) before adding the second monomer mixture to it and carrying out the second-stage polymerization. Alternatively, the first-stage polymerization may be carried out in a reactor and then, without recovering or purifying the resulting polymer, the second monomer mixture may be added to the same reactor and the second-stage polymerization carried out. The second scheme has fewer steps than the first scheme (because of the elimination of recovery, purification, and possible intermediate storage), but the first scheme allows for better quality control of the characteristics of the intermediate polymeric product. Which scheme is used will depend upon a variety of factors, including cost and the need to control the characteristics of the intermediate polymeric product.

Recovery and purification of the intermediate polymer from the first reaction stage (if desired) and recovery and purification of the final polymer from the second reaction stage are accomplished in the following manner. The reaction product is isolated (e.g., removed from the reactor), comminuted, and treated to remove residual reactants. Polymer particle size is usually a few millimeters. Particles too small are undesirable. A sufficient amount of unreacted monomer is removed so that the annealed surgical device and the annealable polymeric composition have the desired properties (e.g., high enough distortion temperature and a high enough molecular weight).

Any method capable of removing the unreacted monomers may be used, provided that method results in the polymeric product having the desired properties and does not adversely affect any other important properties of the final polymer. The preferred purification procedure is as follows.

After comminution, the crude reaction product is contacted with ethyl ether for about 72 hours in a Soxhlet-type extractor to remove unreacted monomer. Typically, in each stage 4–10% of the starting monomers remain unreacted.

After the extraction period, the partially purified polymer is slowly heated under vacuum from ambient temperature to 130° C. over a period of about 100 hours. The slow rate of heating is important to prevent melting (strictly speaking, flowing together) of the copolymer particles and to remove any water present. Dry inert gas may be used to purge the system, and occasionally the heating step may require more than 100 hours for the polymer to reach the desired properties. This procedure removes any residual solvent (ethyl ether) present.

After removal of unreacted monomers (and of solvent, if solvent extraction is used), the purified copolymer must be dried if it was not dried enough in the monomer removal step and, in any event, stored to keep it dry. The intermediate and final polymers must be as dry as possible before forming surgical devices from the final composition because the presence of too much water in the polymers results in inherent viscosity (molecular weight) dropping below the minimum acceptable levels during forming the surgical device. Generally, it is desired that the polymers be dried to a dry state and stored at a relative humidity of no more than a few percent. Preferably, the purified dried polymers (intermediate, if any, and final) are stored under a vacuum and/or with a dry inert gas pad. As will be understood by one skilled in the art, the length of storage affects the allowable relative humidity for storage, higher humidity levels being more acceptable if storage is to be for a shorter period of time.

The two-phase composition of this invention having a continuous lactide-rich phase and a discrete particle glycolide-rich phase may be made by forming the polymers of the two phases separately and then mixing small particles of the glycolide-rich polymer into the lactide-rich polymer. Mixing may be accomplished in conventional equipment (provided the polymeric mateirals are kept dry enough), for example, in the surgical device-forming equipment.

Each polymer may be made separately in the manner described above and then the glycolide-rich polymer comminuted to a fine particle size (generally 10 microns or less) before mixing. Smaller particles give better results. A long grinding period is usually disadvantageous because during grinding, the glycolide-rich polymer may pick up too much moisture from the ambient atmosphere (even if grinding is performed in a dry room), and that will adversely affect the properties of the final device. Accordingly, it is preferred that the glycolide-rich phase be polymerized using a technique that results in the particles being small enough so that a comminuting step is relatively short or not needed at all.

Whichever two-phase composition is used (continuous/continuous or continuous/discrete), the absorbable devices are made preferably by injection molding the final, purified, two-phase polymeric composition using, for example, a screw injection molding machine. The resulting devices have a first phase containing about 0 - about 25%m glycolide moieties and overall composition of up to 45%m glycolide moieties and the first phase constitutes at least 50% (and preferably not more than about 95%) by weight of the devices.

A preheated vacuum hopper retrofitted to the screw injection molding machine has been found to be useful for maintaining the purified dried copolymer in a dry condition. The vacuum hopper comprises a vessel upstream of the machine's standard hopper. The vessel must be capable of operating under vacuum and of being heated.

The preferred procedure for injection molding the device is to place the purified dried copolymer particles in the vacuum hopper under a vacuum, heat the hopper to 50°–70° C., and hold temperature and vacuum for at least an hour, preferably about 15 hours. The pressure in the vacuum hopper is desirably no higher than 5 mm Hg and preferably no higher than 0.1 mm Hg. The standard hopper must also be heated and dried before allowing the purified, dried two-phase polymeric composition to pass from the vacuum hopper into the standard hopper. The entire injection molding system desirably is padded and/or purged with a dry inert gas. Injection molding is generally carried out at a temperature below the melting point of the glycolide-rich phase.

The design of the surgical devices is not critical insofar as the present invention is concerned. The devices may, for instance, be staples or clips. Examples of staples and clips which can be made from the polymers of this invention are shown in U.S. Pat. Nos. 4,060,089 and 4,402,445 and in U.S. pat. appln. Ser. Nos. 429,249 now U.S. Pat. No. 4,492,232 and 429,250, now U.S. Pat. No. 4,512,345 both filed on September 30, 1982, all of which patents and applications are hereby incorporated by reference. Other possible device designs will be known to those skilled in the art.

The formed devices are then annealed (or heat-treated), preferably while held in restraining fixtures, e.g., molds. Holding them in restraining fixtures prevents the annealing step from deforming the devices. The devices are held at 80° to 130° C. for from 10 to 120 minutes, shorter times being used with higher temperatures. The temperature may be held constant at a single value or held constant at two or more values in stages. For a preferred polymeric composition having about 10%m glycolide moieties in the lactide-rich phase and about 35%m glycolide moieties overall, the devices are annealed preferably by keeping them at about 90° C. for about 90 minutes.

Injection molding reduces the crystallinity of the lactide-rich phase from 5–10% to about zero but usually has no effect on the crystallinity of the glycolide-rich phase, which is about 1–5%. Annealing imparts crystallinity to the lactide-rich phase (raising it to about 10–20%) but has little effect on the glycolide-rich phase (crystallinity rises, if at all, to a maximum of about 10%). These crystallinities are calculated based on the entire composition using x-ray diffraction.

A preferred procedure for making the two-continuous-phase composition according to the first scheme (recovery and purification of the intermediate polymer product) is as follows. This discussion describes manufacture of a particular composition having about 10%m glycolide in the lactide-rich phase and about 30%m glycolide moieties overall. The quantities of reactants given may be varied depending on the particular composition desired.

Lactide (5,620 grams) and glycolide (503 grams) are charged to a reactor under an argon blanket. A solution of stannous octoate catalyst in diethyl ether is added to give 0.02% w of catalyst, based on the total weight of lactide and glycolide. Sufficient initiator (pure glycolic acid) is added to control the molecular weight so the desired inherent viscosity is achieved. The reactor is further purged with argon and held at 5 psi while heating to 170°–175° C. Pressure and temperature are maintained for six hours. The reaction product is then recovered and purified in the manner described above.

The intermediate polymeric product is carefully dried in a vacuum oven ($\geq 1$ mm Hg) by heating at 70° C. for 6 hours and then 100° C. for 6 hours. The polymer is allowed to cool to ambient temperature in the vacuum oven. The initial inherent viscosity of the copolymer should be at least 1.9, preferably 2.2. Lower inherent viscosities (e.g., 1.3) may be used if the polymeric product is kept very dry up through the device-forming step. After forming the absorbable surgical device, the inherent viscosity of the device should be $\geq 1.0$, preferably $\geq 1.2$. Inherent viscosity is measured at 30° C. at a concentration of 0.25 g of polymer/dl of solution in a suitable solvent, such as chloroform for the first-stage polymer or hexafluoroisopropanol for the two-phase composition, using a Ubbelohde viscometer.

After cooling, 1,362 grams of polymer (still in the vacuum oven) are transferred to a dry room (temperature 20° C., relative humidity of less than 10%). A 4-quart conical/vertical reactor made by Atlantic Research Corporation (model 4CV) is dried by heating to 120° C. or more under a nitrogen or argon flow and is placed in the dry room.

The vacuum in the oven is released by bleeding in argon. The copolymer is quickly loaded into the reactor while argon is flowing through the reactor. The reactor is sealed, pressurized to about 5 psi, and connected to a temperature controller, hot oil circulator, and an argon tank. The settings on the temperature controller and hot oil circulator are maintained at about 180°–190° C. When the pot temperature reaches 170° C., stirring is started. As soon as a homogeneous melt is obtained and pot temperature is 175°–180° C., 320 grams of purified glycolide are added (430 grams of glycolide if the preferred composition with an overall content of 35%m glycolide moieties is to be made).

When glycolide addition is completed, the reactor is resealed, repressurized, and the stirring rate is increased. When the pot temperature reaches 180° C., the stirring rate is reduced. If the pot temperature continues to rise, the oil bath temperature is reduced to 175° C., 30–60 minutes after addition of the glycolide is complete, the two-phase polymer composition is removed from the reactor and is ground, dried, and ether extracted as described above.

The preferred scheme for making the two-continuous-phase polymeric composition using the second scheme (no removal or purification of the intermediate polymer) is illustrated by the following two examples.

In the first example, purified L-lactide (1,362 grams, 9.4583 gmoles) with 0.02% by weight stannous octoate is placed in a clean and dry reactor (the same type of conical/vertical reactor as described above), which is then sealed and pressurized to about 5 psi with a dry, inert gas (argon or nitrogen). The lactide is polymerized for 14 hours at 155°–160° C. The temperature is then raised to 175°–180° C. and 731.4 grams (6.3056 gmoles) of purified glycolide are added. The mixture is vigorously stirred until the temperature rises to 180° C. and then stirring is slowed to a low speed. The reaction mixture is held at 180°–185° C. for 50–60 minutes, and then the two-phase polymer is removed from the reactor, ground, and extracted as described above to remove residual monomer. The overall molar ratio of monomers used is 40/60 glycolide/L-lactide. The glycolide content of the lactide-rich phase is about 5%m and the overall glycolide content of the final, two-phase composition is about 40% m.

In a second example of the second scheme for making the two-continuous-phase composition, purified L-lactide (1,250.1 grams, 8.6813 gmoles) and purified glycolide (111.9 grams, 0.9646 gmoles) with 0.02% by weight stannous octoate are placed in a clean and dry conical/vertical reactor, which is then sealed and pressurized to about 5 psi with a dry, inert gas (argon or nitrogen). The mixture is polymerized for 14 hour at 155°–160° C. The temperature is then raised to 175°–180° C. and 430.4 grams of purified glycolide (3.7103 gmoles) are added. The mixture is vigorously stirred until the temperature rises to 180° C. and then stirring is slowed to a low speed. The reaction mixture is held at 180°–185° C. for 30–60 minutes and then the copolymer is removed from the reactor, ground, and extracted as described above to remove residual monomer. The overall molar ratio of monomers used is 35/65 glycolide to L-lactide. The glycolide moiety content of the lactide-rich phase is about 10%m and the overall glycolide moiety content of the final, two-phase composition is about 35%m.

In the preferred continuous/discrete two-phase composition, the discrete phase is preferably 100% polyglycolic acid (i.e., 100% m derived from glycolide moieties) of small particle size (generally less than 10 microns). A preferred way of making those particles is as follows. This discussion assumes manufacture of a specific quantity of small particle size polyglycolic acid. Other quantities may be made by modifying the procedure.

1,500 milliliters of toluene are placed in a 4-neck, 3-liter round bottom flask equipped with a heating mantle and a stirrer in the center neck. Two other stirrers are placed in two of the other necks to act as baffles. A thermowell for a thermocouple is placed in the fourth neck for temperature control.

The toluene is heated to 100° C. (with stirring). 500 to 520 grams of pure glycolide are added and the solution temperature is brought back up to 100° C. 3 grams of stannous octoate in 10 cc of toluene are added via syringe. The reaction mixture should be well stirred. A white precipitate will form within a few minutes.

A well-mixed solution of 10 grams of stannous octoate, 10 grams of lauryl alcohol, and 80 cc of toluene is prepared and 10 cc of it are added via syringe to the reaction mixture every 30 minutes. The heating mantle is removed from the reaction flask after the last addition and the reaction mixture is allowed to cool to approximately 50° C.

A fine white powder will be dispersed in the reaction mixture. The powder is recovered by filtration and extracted with boiling acetone for 15 minutes. The powder is filtered and washed with ethyl ether. The ether is removed from the powder by vacuum filtration and the powder is dried in a vacuum oven at 100° C. and less than 10 mm Hg for about 10–15 hours. The powder is comminuted in a ball mill with 7–10 ceramic balls for about 1 hour. The ground particles are screened to remove any large agglomerates and are then blended with a lactide-rich polymer and injection molded to form the surgical devices.

Two-continuous-phase compositions were made using the first scheme (intermediate polymer recovery and purification) and tested to show the advantages of this invention. The results are reported in the following tables. In those tables, the glycolide moiety contents of the two-phase polymeric compositions are indicated by a four-digit code, for example "1030." The first two digits ("10") indicate the glycolide moiety concentration in the monomer mixture used to make the lactide-rich phase and the last two digits ("30") indicate the overall glycolide moiety concentration in the monomer mixtures used to make the entire two-phase composition. For that example the glycolide moiety concentrations of the lactide-rich phase and overall are approximately 10% m and 30% m, respectively.

Table I shows the tensile strengths of the hinge portion, the crystallinities (as measured by x-ray diffraction), the approximate distortion temperatures, and the times to failure in hot-wet creep tests of surgical clips having essentially the configuration shown in U.S. pat. appln. Ser. No. 429,250, filed Sept. 30, 1982 now U.S. Pat. No. 4,512,345, made of different annealed and unannealed two-phase compositions and of two "control" compositions. Each control composition is a one-phase, substantially amorphous material made by the method disclosed in U.S. pat. appln. Ser. No. 436,056, filed Oct. 22, 1982 now U.S. Pat. No. 4,523,591. Control composition I contains approximately 20%m glycolide moieties and 80%m lactide moieties and control composition II contains approximately 30%m glycolide moieties and 70%m lactide moieties.

The tensile strengths were measured using an Instron tester at a crosshead speed of 0.02 inches per minute. The time to failure in the hot-wet creep test is the time required for the clip to fail, that is, allow air to pass through an externally clipped flexible tube, when the tube is subjected to an internal 2 psi pressure applied at one-hour intervals. Between pressurizations, the clip is immersed in water at 103° F.

TABLE I

| Material | Tensile Strength (psi) At Peak Load | Tensile Strength (psi) At Yield Load | Crystallinity (%) L-Rich Phase | Crystallinity (%) G-Rich Phase | Crystallinity (%) Overall | Distortion Temp. (°F.) | Hot-Wet Creep Failure (hours) |
|---|---|---|---|---|---|---|---|
| Control I | 7330 ± 670 | 5200 ± 800 | — | — | 5 | 125 | 3–5 |
| Control II | — | — | — | — | — | <125 | — |
| 1030 (unannealed) | 6920 ± 850 | 5100 ± 300 | 0 | 1–2 | 1–2 | 130 | 4–6 |
| 1030 (annealed) | 9020 ± 380 | 5400 ± 600 | 7.5–15 | 3–6 | 10.5–21 | >160 | >72 |
| 1035 (unannealed) | 7640 ± 330 | 5600 ± 600 | 0 | 2.5–5 | 2.5–5 | 135 | 6–8 |
| 1035 (annealed) | 8760 ± 310 | 6600 ± 1300 | 10–20 | 3–6 | 13–26 | >160 | >72 |

The results show that annealing significantly increases the tensile strength of surgical devices made from the new two-phase composition. The results also show that annealing has little effect on the crystallinity of the glycolide-rich phase but a significant effect on the crystallinity of the lactide-rich phase. The results also show that annealed surgical devices made of the new multi-phase composition have significantly higher distortion temperatures than devices made of a substantially amorphous composition having the same overall composition (compare Control II with "1030 annealed"). The results also show the superior hot-wet creep resistance of the annealed devices of this invention.

The following table shows how annealing affects the rate of loss of peak tensile strength of surgical staples made using the compositions of this invention and made using the control compositions. The staple configuration is substantially the same as that shown in U.S. pat. appln. No. 480,423, filed Mar. 30, 1983 now U.S. Design Pat. No. D280931, which application is hereby incorporated by reference. For the in vitro tests, the staples were placed in a buffer solution (pH=7.0) at 37° C. After 7 and 14 days, several staples were withdrawn and tested using an Instron tester (cross-head speed of 0.02 inches/minute). For the in vivo tests, staples were implanted in abdominal and muscular tissues in rats (two staples per rat). After 14 and 21 days each, five rats were sacrificed and the staples were removed and tested using an Instron tester (cross-head speed of 0.02 inches/minute). The in vivo tensile strengths shown below are averages of the abdominal and muscular values.

TABLE II

| | Percentage Of Initial Tensile Strength Remaining | | | | |
|---|---|---|---|---|---|
| | | In Water | | In Rats | |
| Material | Initial | 7 days | 14 days | 14 days | 21 days |
| Control I | 100 | 100 | 100 | >100 | >100 |
| Control II | 100 | — | — | 52 | 27 |
| 0040 (unannealed) | 100 | 63 | 49 | 37 | 40 |
| 0040 (annealed) | 100 | — | — | — | — |
| 1030 (unannealed) | 100 | 99 | 86 | — | — |
| 1030 (annealed) | 100 | 73 | 43 | — | — |
| 1035 (unannealed) | 100 | 92 | 81 | — | — |
| 1035 (annealed) | 100 | 49 | 33 | 33 | 10 |

The results show that annealing significantly increases the in vitro rate of loss of tensile strength. Other tests have shown that for the compositions of this invention, rate of loss of tensile strength in vitro is an excellent predictor of and closely matches the rate of loss of tensile strength in vivo.

Many modifications and variations in the new invention may be made. For example, the new composition has been described as being two-phase. It is possible that three or more stages of monomer addition and polymerization could be used. The resulting multi-phase polymer would then have more than two phases. However, it still should have a lactide-rich first phase constituting at least 50% by weight of the total composition and have no more than about 25%m glycolide moieties. The two or more other phases would then have lactide and glycolide moieties in amounts such that the overall multi-phase composition had no more than about 45%m glycolide moieties.

Another possible variation when preparing an interpolymer composition of this invention (all phases continuous) is to use the crude multi-phase polymeric composition from the final polymerization stage (without any purification) for making the surgical devices.

Another possible variation is to interpolymerize several continuous phases, but also add one or more discrete phases.

Other modifications and variations will be apparent to those skilled in the art and the claims are intended to cover all such modifications and variations that fall within the true spirit and scope of the invention.

We claim:

1. A process for making a surgical device, comprising the steps:
   (a) polymerizing a first monomer mixture containing a predominant amount of lactide until the polymerization is substantially complete, thereby forming a first polymer in a first phase;
   (b) adding to the first polymer a second monomer mixture containing glycolide and polymerizing the second monomer mixture in the presence of the first polymer, thereby forming a final polymer having two phases;
   (c) recovering the final polymer from the final polymerization stage;
   (d) forming a surgical device from the final polymer; and
   (e) annealing the surgical device wherein lactide moieties comprise at least 50% by weight of the annealed surgical device;
   (f) the quantities of monomers being chosen so that (i) one phase of the final polymer has from about 0 - about 25%m glycolide moieties and about 75 - about 100% m lactide moieties and (ii) the final polymer overall has up to 45%m glycolide moieties.

2. The process of claim 1 wherein annealing is carried out at from 80° to 130° C. for from 10 to 120 minutes.

3. The process of claim 1 wherein annealing is carried out at about 90° C. for about 90 minutes.

4. A process for making a surgical device, comprising the steps:
   (a) polymerizing a first monomer mixture containing a predominant amount of lactide until the polymerization is substantially complete, thereby forming a first polymer in a first phase;
   (b) adding to the first polymer a second monomer mixture containing glycolide and polymerizing the second monomer mixture in the presence of the first polymer, thereby forming a final polymer having two phases and a predominant amount of lactide;
   (c) recovering the final polymer;
   (d) forming a surgical device by injection molding the final polymer at a temperature below the melting point of the glycolide-rich phase.

5. The process according to claim 4 wherein annealing is carried out at from 80°-130° C. for from 10 to 120 minutes.

6. The process according to claim 4 wherein the first polymer is composed of lactide moieties.

7. The process according to claim 4 wherein one phase of the final polymer has from about 0-about 25% m glycolide moieties and about 75-about 100% lactide moieties.

8. The process according to claim 4 wherein the surgical device is a surgical clip or staple.

9. A process for making a surgical device, comprising the steps:
   (a) polymerizing a first monomer mixture containing a predominant amount of lactide until the polymerization is substantially complete, thereby forming a first polymer;
   (b) adding to the first polymer a second monomer mixture containing glycolide and polymerizing the second monomer mixture in the presence of the first polymer, thereby forming a final polymer having two phases and a predominant amount of lactide;
   (c) recovering the polymer;
   (d) forming a surgical device from the final polymer; and
   (e) annealing the surgical device.

10. The process according to claim 9 wherein annealing is carried out at from 80°-130° C. for from 10 to 120 minutes.

11. The process according to claim 9 wherein the first polymer is composed of lactide moieties.

12. The process according to claim 9 wherein one phase of the final polymer has from about 0 - about 25%m glycolide moieties and about 75 - about 100% lactide moieties.

13. The process according to claim 9 wherein the surgical device is a clip or staple.

* * * * *